US009820977B2

(12) United States Patent
Johnson et al.

(10) Patent No.: US 9,820,977 B2
(45) Date of Patent: Nov. 21, 2017

(54) SYSTEMIC TREATMENT OF BLOOD-SUCKING AND BLOOD-CONSUMING PARASITES BY ORAL ADMINISTRATION OF A PARASITICIDAL AGENT

(75) Inventors: Roland H. Johnson, Lexington, NC (US); Douglas I. Hepler, McLeansville, NC (US); Kathleen G. Palma, McLeansville, NC (US); William R. Campbell, Jamestown, NC (US)

(73) Assignee: BAYER HEALTHCARE LLC, Shawnee, KS (US)

( * ) Notice: Subject to any disclaimer, the term of this patent is extended or adjusted under 35 U.S.C. 154(b) by 0 days.

(21) Appl. No.: 12/471,129

(22) Filed: May 22, 2009

(65) Prior Publication Data

US 2010/0087492 A1 Apr. 8, 2010

Related U.S. Application Data

(60) Provisional application No. 61/102,774, filed on Oct. 3, 2008.

(51) Int. Cl.
    *A61K 31/44* (2006.01)
    *A61K 31/4439* (2006.01)
    *A61K 9/00* (2006.01)

(52) U.S. Cl.
    CPC ............ *A61K 31/44* (2013.01); *A61K 9/0056* (2013.01)

(58) Field of Classification Search
    None
    See application file for complete search history.

(56) References Cited

U.S. PATENT DOCUMENTS

| | | | | |
|---|---|---|---|---|
| 5,712,295 A * | 1/1998 | Mencke et al. | | 514/338 |
| 2004/0037869 A1* | 2/2004 | Cleverly et al. | | 424/442 |
| 2005/0158367 A1* | 7/2005 | Hershberger | | 424/442 |
| 2006/0057178 A1 | 3/2006 | Borchert et al. | | |
| 2006/0105009 A1* | 5/2006 | Bregante | | 424/405 |
| 2007/0293446 A1* | 12/2007 | Soll et al. | | 514/27 |
| 2011/0263641 A1* | 10/2011 | Lahm et al. | | 514/307 |

FOREIGN PATENT DOCUMENTS

| | | |
|---|---|---|
| CN | 1 386 420 A | 12/2006 |
| EP | 0 966 961 A1 | 12/1999 |
| EP | 1 634 584 A1 | 3/2006 |
| JP | A H10-500699 | 1/1998 |
| JP | 2000-062271 | 2/2000 |
| JP | 2003 081719 A | 3/2003 |
| JP | A 2005-515215 | 5/2005 |
| JP | 3759739 | 3/2006 |
| JP | A 2007-532683 | 11/2007 |
| RU | 2002124584 A | 10/2004 |
| WO | 0111963 A1 | 2/2001 |
| WO | 2006050772 A1 | 5/2006 |
| WO | 2006077070 A1 | 7/2006 |

OTHER PUBLICATIONS

Solecki R., Pesticide residues in food, the International Programme on Chemical Safety (IPCS) INCHEM, Toxicological Evaluations, IMIDACLORPID, Joint Meeting on Pesticide Residues (JMPR), pp. 1-28 (2001).*
Dryden et al., Vet. Ther., 6(3): 228-236, Fall 2005.*
Dryden et al., "Comparative speed of kill of selamectin, imidacloprid, and fipronil-(S)-methoprene spot-on formulations against fleas on cats", pp. 1-5 (originally appeared in Vet. Ther., 6(3):228-236, Fall 2005).
Makhteshim-Agan of North America, Inc., Material Safety Data Sheet for Imidacloprid 4F, pp. 1-5 (2005).
Solecki R., Pesticide residues in food, the International Programme on Chemical Safety (IPCS) INCHEM, Toxicological evaluations, IMIDACLOPRID, Joint Meeting on Pesticide Residues (JMPR), pp. 1-28 (2001).
Imidacloprid. *Risk characterization document/Dietary and drinking water exposure.* Feb. 9, 2006, p. 6, 14, 16, 21. Internet: http://www.cdprca.gov/docs/risk/rcd/imidacloprid.pdf).
Mehlhorn H., et al. *Effects of imidadoprid on adult and larval stages of the flea Ctenocephalides fells after in vivo and in vitro application*: Patasitol. Res, 1999, 85: p. 625-637.
Fourie Li, et al. *The efficacy of an imidacloprid/moxidectin combination against naturally acquired Sarcoptes scabiei infestations on dogs.* Aust. Vet. J., 2006, Jan.-Feb., 84 (1-2), p. 17-21 electron-microscopy study. Patasitol. Res, 1999, 85: p. 625-637.
Venco L. et al. *Field efficacy and safety of a combination of moxidectin and imidaclopnd for the prevention of feline heartworm (Dirofilaria immitis) infection* Net. Parasitol. 2008, Jun. 14, 154 (1-2), p. 67-70.
Dryden MW, et al. *Evaluation of an imidaclopnd (8.8% w/w)-permetrin (44.0% w/w) topical spot-on and a fipronil (9.8% w/w)-(S)-methoprene (8.8% w/w) topical spot-on to repel, prevent attachment, and kill adult Ixodes scapularis and Amblyomma americanum ticks on dogs.* Vet. Ther. 2006, 7(3), abstract, p. 173-186.
European Search Report (dated Aug. 24, 2012) EP 09 81 8474.
Russian Office Action (dated Feb. 6, 2013) RU 2011117203.
Japanese Office Action (dated Aug. 29, 2013) JP 2011-530203.

* cited by examiner

*Primary Examiner* — Svetlana M Ivanova

(74) *Attorney, Agent, or Firm* — McBee Moore Woodward & Vanik IP, LLC

(57) ABSTRACT

Pharmaceutically acceptable single parasiticidal agent compositions of imidacloprid for oral delivery to mammals to systemically control targeted blood-sucking or blood-consuming parasites, such as fleas, ticks and certain species of helminthes and scabies.

20 Claims, No Drawings

SYSTEMIC TREATMENT OF BLOOD-SUCKING AND BLOOD-CONSUMING PARASITES BY ORAL ADMINISTRATION OF A PARASITICIDAL AGENT

RELATED APPLICATION

This application is a utility application and claims priority under 35 U.S.C. §119(e) of U.S. provisional application Ser. No. 61/102,774 filed Oct. 3, 2008, the entire content of which is incorporated herein by reference.

FIELD OF THE INVENTION

The invention relates to the oral administration of parasiticidal agents. More particularly, the invention relates to administration of a parasiticidal agent, such as a neonicotinoid, to mammals to treat external blood-sucking and blood-consuming parasites and certain internal blood-sucking or blood-consuming parasites.

BACKGROUND OF THE INVENTION

With the exception of lufenuron, an insect growth regulator, the market for ectoparasite control in mammals has long been dominated by compositions for topical administration. The latter includes the two top-selling topical products for flea and tick control, ADVANTAGE® (imidacloprid) with efficacy against fleas (but not ticks), sold for use on dogs and cats, and FRONTLINE® (fipronil) with efficacy against fleas, ticks and scabies, also sold for use on dogs and cats. Both imidacloprid and fipronil are toxic at relatively low oral dosages. Fipronil is also known to cause emesis when given orally to control fleas, while oral efficacy of imidacloprid against targeted parasites has not been reported. Indeed, even when given topically, imidacloprid alone is reported to have little or no effect on ticks. Instead, a further active admixed with imidacloprid is required, such as the permethrin used in the ADVANTIX® product, which has some efficacy against ticks.

Although these products have efficacy against at least fleas when applied topically, the route of administration raises concerns regarding the active compounds' potentially toxic effect on humans. For both products, it is generally advised that humans not contact the administration site for several hours after application. Compliance with this advice as to treatment of domestic pets can be difficult, especially for children. In addition, the carriers used for such topical products often contain waxes, oils or other spreading agents, and so remain on the treated animal's skin for a length of time sufficient to risk environmental contamination or staining. Furthermore, certain products containing these actives include other agents that are toxic to other species. For example, permethrin is suitable for use in dogs but is potentially lethal to cats, making topical use of such products problematic in multi-species environments.

It is therefore desirable to provide an orally deliverable compound for control of targeted parasites. It is especially desirable to provide such a compound in a readily consumable dosage form.

SUMMARY OF THE INVENTION

The invention is based in part on the surprising discovery that imidacloprid, when given orally at relatively low sub-toxic doses, systemically kills blood-sucking and blood-consuming parasites ("targeted parasites") of mammals quickly and comprehensively, and can do so in the absence of other parasiticidal agents.

The invention therefore provides pharmaceutically acceptable parasiticidal compositions of imidacloprid for oral delivery to mammals to control targeted parasites. The parasiticidal compositions of the invention may be formulated in any suitable oral form; for example, a chewable treat.

In an embodiment of the invention, the targeted parasites are adult fleas, adult ticks or tick nymphs. In a further embodiment of the invention, the targeted parasites are flea or tick larvae or eggs.

In a further embodiment of the invention, the targeted parasites are fleas, and the imidacloprid is provided at a single dosage level of 10 mg/kg or less, with dosages as low as about 0.25 mg/kg being sufficient to eliminate an infestation from the treated animal within 1-24 hours of dosing. Optionally, dosing may be repeated at the same or higher dosage (up to 10 mg/kg) to control or prevent reinfestation.

In a further embodiment of the invention, the targeted parasites are ticks, tick nymphs or tick eggs, and the imidacloprid is provided at a single dosage level of 30 mg/kg or less, with dosages as low as about 3.0 mg/kg being sufficient to eliminate an infestation from the treated animal within 1-72 hours of dosing. Optionally, dosing may be repeated at the same or higher dosage (up to 30 mg/kg) to control or prevent reinfestation.

In a further embodiment of this aspect of the invention, the imidacloprid composition is orally administered as often as necessary to control the parasites. It can be reasonably expected that at least about 60% of all adult ticks and tick nymphs will be killed within 1-24 hours following administration of a single dose in accord with the invention, and that about 100% of all adult fleas will be killed within 1-24 hours following administration of a single dose in accord with the invention.

The invention further relates to use of fipronil as an oral parasiticidal agent, when given orally at doses that are sub-toxic to the treated animals, kills targeted parasites quickly, comprehensively and without emesis when provided in certain oral dosage formats. The invention therefore provides pharmaceutically acceptable compositions of fipronil for oral delivery to mammals to control targeted parasites.

In another embodiment of this aspect of the invention, the targeted parasites are adult fleas, adult ticks or tick nymphs. In a further embodiment of the invention, the targeted parasites are flea or tick larvae or eggs.

In a further embodiment of this aspect of the invention, the parasiticidal agent present in the pharmaceutical composition is fipronil, without derivation or modification of the compound. In another aspect of this embodiment, this fipronil active is the only parasiticidal agent present in the pharmaceutical composition.

In a further embodiment of the invention, the targeted parasites are blood-sucking or consuming helminthes.

DESCRIPTION OF THE INVENTION

A. Active Ingredients of the Pharmaceutically Acceptable Parasiticidal Compositions of the Invention.

By "pharmaceutically acceptable parasiticidal composition" and "parasiticidal composition" it is meant that the active parasiticidal agent present is formulated for oral delivery in a manner rendering the composition product acceptable for administration to warm-blooded mammals (humans or animals). The preferred parasiticidal active agents are the central nervous system active neonicotinoids, a class that includes acetamiprid, clothianidin, dinotefuran, imidacloprid, nitenpyram, thiacloprid and thiamethoxam. The presently preferred neonicotinoid active is imidacloprid, whose chemical formula follows:

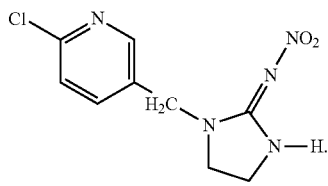

Imidacloprid: E or Z isomer (preferably E) of 1-[(6-chloro-3-pyridinyl)methyl]-N-nitro-2-imidazolidinimine Those of ordinary skill in the art will recognize that modifications to neonicotinoid compounds compound are possible, such as pegylation. Substitutents may also be introduced to the compound. However, the introduction of substituents including halogens, alkoxy groups, alkyls and others into the 5-position of the pyridine ring of imidacloprid in particular may reduce imidacloprid's neuroblocking activity. The introduction of alkoxy groups at this position may also be unfavorable for activity. As such, imidacloprid without modification of substituents at the 5-position of the pyridine ring might desirably be avoided in the invention. Umnodified, underivatized imidacloprid is highly effective as used according to the invention, and its use is therefore preferred.

Another active class whose use is contemplated by the invention is the phenylpyrazoles, such as fipronil, or its desulfinyl, sulfinyl, sulfide, or sulfone metabolites. The chemical structure of fipronil follows:

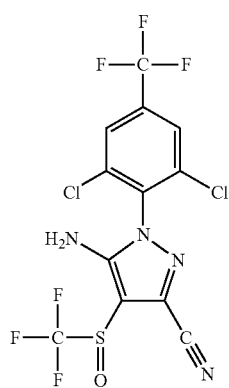 [SMILES: N#Cc1nn(-c2c(Cl)cc(C(F)(F)F)cc2Cl)c(N)c1S(=O)C(F)(F)F]

Fipronil: 5-amino-1-[2,6-dichloro-4-(trifluoromethyl)phenyl]-4-[(trifluoromethyl)sulfinyl]-1H-pyrazole-3-carbonitrile. As noted, certain metabolites of fipronil may also be useful in the invention. However, in a preferred embodiment, it is not necessary to modify the active compound itself to avoid adverse effects on the treated host, such as emesis.

Also, it is not necessary to include other active agents in the pharmaceutically acceptable compositions of neonicotinoids or phenylpyrazoles to achieve the desired level of efficacy.

B. Ectoparasite Targets

The active compounds in the formulations of the invention are suitable for the control of blood-sucking or consuming parasites which can be found in humans and mammalian animals, including domestic animals, productive livestock, zoo animals, laboratory animals, experimental animals and pets, while having favorable toxicity to mammals at the dosages provided by the invention. The productive livestock and breeding animals include mammals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chickens, geese, turkeys and ducks. Laboratory and experimental animals include mice, rats, guinea pigs, golden hamsters, dogs and cats. Pets include dogs and cats.

The pharmaceutical composition is parasiticidally active against all developmental stages of bloodsucking or blood consuming parasites, including larvae, nymphs and eggs. Targeted parasites are those which bite the host or otherwise gain access to its blood during infestation, and include the order Siphonaptera (fleas) extending, for example, to the genera *Ctenocephalides., Echidnophaga, Pulex* and *Ceratophyllus*; the order Ixodida (ticks) including all infraorders, with emphasis on the family Ixodidae extending, for example, to the genera *Ixodes, Dermacentor, Rhipicephalus, Amblyomma, Haemaphysalis* and *Boophilus* as well as the family Argasidae extending, for example, to the genera *Argasinae, Ornithodorinae, Otobinae, Antricolinae* and *Nothoaspinae*; the order Anoplura (blood-sucking lice) extending, for example, to the genera *Haematopinus, Linognathus, Solenopotes, Pediculus* and *Pthirus*; the order Mallophaga (consuming lice) extending, for example, to the genera *Trimenopon, Menopon, Eomenacanthus, Menacanthus, Trichodectes, Felicola, Damalinea* and *Bovicola*; the order Diptera extending, for example, to the consuming species, such as those of the genus *Ceratopogonidae*; the order Astigmata extending, for example, to the genus *Sarcoptes* (in the presence of blood); and the order Strongiloidae extending to those species that bite and/or suck blood, such as hookworms, tapeworms and heartworms.

C. Dosage Forms for the Parasiticidal Comnositions of the Invention.

1. Dosage Ranges.

Parasiticidal control according to the invention can be effected prophylactically as well as therapeutically. To those ends, eradication of a flea infestation can be achieved with a single neonicotinoid dose in the range of 0.01 to 10 mg/kg, preferably about 0.25 to about 0.5 mg/kg, optionally 1, 3, 6 or 10 mg/kg, including all dosages in between the stated ranges. As demonstrated in the Examples, a single dose of parasiticidal composition providing 0.25 mg/kg of imidacloprid was 100% effective against a flea infestation on treated animals within as little as an hour of administration of the dose.

To control against reinfestation without redosing the animal, higher initial dosing with a neonicotinoid is more effective, with the maximal 10 mg/kg level for imidacloprid having greatest effect at one week post-dosing, as illustrated in Table 3 of Example II. However, repeated dosing at lower levels will be as effective, without risk of toxicity. Therefore, parasiticidal compositions of the invention for use against fleas may be provided in single or multiple dose packaging, with each dose being the same or different to achieve the treatment results best suited to a particular case.

Further, eradication of a tick and/or tick nymph infestation can be achieved with a single dose in the range of 0.01 to 30 mg/kg per day. In apparently anomalous results, as illustrated by Example II, Tables 4 and 5, dosing at about the 3 mg/kg level was significantly more effective against a tick infestation than dosing at the 10 mg/kg level, and more effective than dosing at the 15 mg/kg level. As dosing approached the maximal sub-toxic level of 30 mg/kg, efficacy increased to about the same level achieved at the 3 mg/kg level. Therefore, a single dose of parasiticidal composition providing 3 mg/kg of imidacloprid was at least 60% effective against a tick infestation on treated animals within as little as 24-48 hours of administration of the dose.

It can be expected that, as observed with respect to fleas, higher dosages might sustain longer half-lives and therefore a degree of efficacy against reinfestation over longer periods of time than lower dosages. As such, dosing in the 15, 22 or 30 mg/kg levels (and all points in between that range) can be provided to avoid a need for re-dosing, or multiple doses can be provided at lower dosage levels (e.g., 3 mg/kg), without risk of toxicity. Therefore, parasiticidal compositions of the invention for use against ticks may be provided in single or multiple dose packaging, with each dose being the same or different to achieve the treatment results best suited to a particular case.

Effective dosage ranges of the pharmaceutical formulations of a phenylpyrazole compound such as a fipronil composition for oral administration are in the range of 0.01 to 0.3 mg/kg per day, preferably about 0.05 to about 0.3 mg/kg per day.

Following oral administration of the pharmaceutical compositions of the present invention, the active agent passes though the mucosal barriers of the GI tract and is absorbed into the blood stream where it can be detected in the plasma of subjects. The level of active agent in the bloodstream as measured in the plasma is dose-dependent. The active agent facilitates the absorption of the drug (active agent) administered therewith (either in the same dosage form, or simultaneously therewith), or sequentially (in either order, as long as both the active agent and the drug are administered within a time period which provides both in the same location, e.g., the stomach, at the same time). By measuring plasma concentrations and with dose response studies, the daily dosage for the imidacloprid of the invention may be modified for less frequent administration.

2. Dosage Formats.

The parasiticidal compositions of the invention can be provided in any therapeutically acceptable pharmaceutical form. For example, the compositions can be formulated for oral administration as drug powders, crystals, granules, small particles (which include particles sized on the order of micrometers, such as microspheres and microcapsules), particles (which include particles sized on the order of millimeters), beads, microbeads, pellets, pills, microtablets, compressed tablets or tablet triturates, molded tablets or tablet triturates, and in capsules, which are either hard or soft and contain the composition as a powder, particle, bead, solution or suspension. The parasiticidal compositions can also be formulated for oral administration as a solution or suspension in an aqueous liquid, as a liquid incorporated into a gel capsule or as any other convenient formulation for administration, or for rectal administration, as a suppository, enema or other convenient form. The parasiticidal composition can also be provided as a controlled release system (see, e.g., Langer, 1990, *Science* 249: 1527-1533).

As to oral dosage forms of the present invention that are solid, the active may simply be provided in gelatin capsules, with or without optional pharmaceutical excipients. Suitable pharmaceutical excipients are known to those of ordinary skill in the art and include, in addition to those mentioned with respect to the chewable treat dosage form, the following: acidifying agents (acetic acid, glacial acetic acid, citric acid, fiumaric acid, hydrochloric acid, diluted hydrochloric acid, malic acid, nitric acid, phosphoric acid, diluted phosphoric acid, sulfuric acid, tartaric acid); aerosol propellants (butane, dichlorodifluoro-methane, dichlorotetrafluoroethane, isobutane, propane, trichloromonofluoromethane); Air displacements (carbon dioxide, nitrogen); alcohol denaturants (denatonium benzoate, methyl isobutyl ketone, sucrose octacetate); alkalizing agents (strong ammonia solution, ammonium carbonate, diethanolamine, diisopropanolamine, potassium hydroxide, sodium bicarbonate, sodium borate, sodium carbonate, sodium hydroxide, trolamine); anticaking agents, such as glidants; antifoaming agents (dimethicone, simethicone); antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); capsule lubricants (see tablet and capsule lubricant); chelating agents (edetate disodium, ethylenediaminetetraacetic acid and salts, edetic acid); coating agents (sodium carboxymethyl-cellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, camauba wax, microcystalline wax, zein); colorants (caramel, red, yellow, black or blends, ferric oxide); complexing agents (ethylenediaminetetraacetic acid and salts (EDTA), edetic acid, gentisic acid ethanolmaide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); glidants and/or anticaking agents (calcium silicate, magnesium silicate, colloidal silicon dioxide, talc); humectants (glycerin, hexylene glycol, propylene glycol, sorbitol); plasticizers (castor oil, diacetylated monoglycerides, diethyl phthalate, glycerin, mono- and di-acetylated monoglycerides, polyethylene glycol, propylene glycol, triacetin, triethyl citrate); polymers (e.g., cellulose acetate, alkyl celloloses, hydroxyalkylcelloloses, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); sorbents (powdered cellulose, charcoal, purified siliceous earth); crbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); tablet binders (acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, corspovidone, polacrilin potassium, sodium starch glycolate, starch, pregelatinized starch); gablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); toriicity agents (dextrose, glycerin, mannitol, potassium chloride, sodium chloride); flavoring vehicles, including flavored and/or sweetened fluids (aromatic elixir, compound benzaldehyde elixir, isoalcoholic elixir, peppermint water, sorbitol solution, syrup, tolu balsam syrup); oil vehicles, (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); carrier vehicles (sugar spheres); viscosity-increasing agents (see suspending agent); water repelling agents (cyclomethicone, dimethicone, simethicone); and wetting and/or solubilizing agents (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol). This list is not meant to be exclusive, but instead merely representative of the classes of excipients and the particular excipients which may be used in any oral dosage forms of the present invention.

The parasiticidal compositions of the invention may also be formulated to have an enteric coating along with another pharmaceutically acceptable vehicle. For example, a ablet can be formed by compression of the composition, without excipients, into a tablet of pharmaceutically acceptable hardness and friability), optionally with a lubricant (e.g., magnesium stearate) and enteric coated.

Polymers which are useful for the preparation of enteric coatings include, but are not limited to, shellac, starch and amylose acetate phthalates, styrene-maleic acid copolymers, cellulose acetate succinate, cellulose acetate phthalate (CAP), polyvinylacetate phthalate (PVAP), hydroxypropylmethylcellulose phthalate (grades HP-50 and HP-55), ethylcellulose, fats, butyl stearate, and methacrylic acid-methacrylic acid ester copolymers with acid ionizable groups ("EUDRAGIT™"), such as "EUDRAGIT™ L 30D", "EUDRAGIT™ RL 30D", "EUDRAGIT™ RS 30D", "EUDRAGIT™ L 100-55", and "EUDRAGIT™ L 30D-55".

The disintegration of the enteric coating occurs either by hydrolysis by intestinal enzymes or by emulsification and dispersion by bile salts, depending upon the type of coating used. For example, esterases hydrolyze esterbutyl stearate to butanol and stearic acid and, as the butanol dissolves, the stearic acid flakes off of the medicament. Additionally, bile salts emulsify and disperse ethylcellulose, hydroxypropylmethylcellulose, fats and fatty derivatives. Other types of coatings are removed depending on the time of contact with moisture, for example coatings prepared from powdered carnauba wax, stearic acid, and vegetable fibers of agar and elm bark rupture after the vegetable fibers absorb moisture and swell. The time required for disintegration depends upon the thickness of the coating and the ratio of vegetable fibers to wax.

Application of the enteric coating to the parasiticidal composition can be accomplished by any method known in the art for applying enteric coatings. For example, but not by way of limitation, the enteric polymers can be applied using organic solvent based solutions containing from 5 to 10% w/w polymer for spray applications and up to 30% w/w polymer for pan coatings. Solvents that are commonly in use include, but are not limited to, acetone, acetone/ethyl acetate mixtures, methylene chloride/methanol mixtures, and tertiary mixtures containing these solvents. Some enteric polymers, such as methacrylic acid-methacrylic acid ester copolymers can be applied using water as a dispersant. The volatility of the solvent system must be tailored to prevent sticking due to tackiness and to prevent high porosity of the coating due to premature spray drying or precipitation of the polymer as the solvent evaporates.

Furthermore, plasticizers can be added to the enteric coating to prevent cracking of the coating film. Suitable plasticizers include the low molecular weight phthalate esters, such as diethyl phthalate, acetylated monoglycerides, triethyl citrate, polyethyl glycoltributyl citrate and triacetin. Generally, plasticizers are added at a concentration of 10% by weight of enteric coating polymer weight. Other additives such as emulsifiers, for example detergents and simethicone, and powders, for example talc, may be added to the coating to improve the strength and smoothness of the coating. Additionally, pigments may be added to the coating to add color to the pharmaceutical formulation.

In general, the parasiticidal compositions of the invention can also be prepared in granulated or powder form (e.g., for use in a feed-through dosing regimen) using any method known in the art, such as but not limited to, crystallization, spray-drying or any method of comminution, including wet or dry granulation. Granulating agents which are useful for preparing the parasiticidal composition granules, include but are not limited to, cellulose derivatives (including carboxymethylcellulose, methylcellulose, and ethylcellulose), gelatin, glucose, polyvinylpyrrolidone (PVP), starch paste, sorbitol, sucrose, dextrose, molasses, lactose, acacia gum, sodium alginate, extract of Irish moss, panwar gum, ghatti gum, mucilage of isapol husks, Veegum and larch arabogalactan, polyethylene glycol, and waxes. Granulating agents may be added in concentrations ranging from 1 to 30% of the mass of the particles or granules.

Parasiticidal composition granules or powder particles can also be suspended in a solution for oral administration as a liquid. The suspension can be prepared from aqueous solutions to which thickeners and protective colloids are added to increase the viscosity of the solution to prevent rapid sedimentation of the coated powder particles or granules. Any material which increases the strength of the hydration layer formed around suspended particles through molecular interactions and which is pharmaceutically compatible with the parasiticidal composition can be used as a thickener, such as but not limited to, gelatin, natural gums (e.g., tragacanth, xanthan, guar, acacia, panwar, ghatti, etc.), and cellulose derivatives (e.g., sodium carboxymethylcellulose, hydroxypropylcellulose, and hydroxypropylmethylcellulose, etc.). Optionally, a surfactant such as Tween may be added to improve the action of the thickening agent.

The parasiticidal compositions of the invention may also be formulated or administered with a non-parasiticidal substance that inactivates or inhibits the action of stomach enzymes, such as pepsin. Alternatively, the pharmaceutical composition containing the parasiticidal composition is administered either concurrent with or subsequent to administration of a pharmaceutical composition active to inactivate or inhibit the action of stomach enzymes. For example, but not by way of limitation, protease inhibitors, such as aprotin, can be used to inactivate stomach enzymes. In another embodiment, the parasiticidal composition is formulated or administered with a compound or compounds which inhibit the secretion of stomach acid. Compounds which are useful for inhiconsuming the secretion of stomach acid include, but are not limited to, ranitidine, nizatidine, famotidine, cimetidine, and misoprostol.

One especially useful delivery format for animals is the soft (mildly friable under pressure) chewable treat for edible consumption. Preferably, a manufacturing process is utilized to produce edible soft treats for delivery of the parasiticidal compositions of the invention wherein the blending of actives into the chew mixture is achieved without generation of heat at a level that would cause the active to wholly or partially degrade. The method is preferably performed so the chew mixture and formed treats are not exposed to temperatures at or above those typically generated by compression and/or shear stress exerted in extrusion, which may be measured by means known to those of ordinary skill in the manufacturing arts (see, e.g., Vermeulen et al., *Chemical Engineering Science* (1971) 26: 1445-1455; Chung et al., *Polymer Engineering and Science* (1977) 17: 9-20; Mount et al., *Polymer Engineering and Science* (1982) 22(12): 729-737; Lindt, J. T., *Conference Proceedings, ANTEC '84, Society of Plastics Engineers* (1984) 73-76; Rauwendaal, C., *Conference Proceedings, ANTEC '93, Society of plastics Engineers* (1993) 2232-2237; Miller et al., *Conference Proceedings, ANTEC '74, Society of Plastics Engineers* (1974) 243-246; Derezinski, S. J., *Conference Proceedings, ANTEC '88, Society of Plastics Engineers* (1988) 105-108; Derezinski, S. J., *Journal of Materials Processing & Manufacturing Science* (1997) 6(1): 71-77; Derezinski, S. J., *Conference Proceedings, ANTEC '96, Society of Plastics Engineers* (1996) 417-421).

In one aspect of the preferred soft treat manufacturing process, the chew mixture and formed treats are not exposed to temperatures of more than about 10° above room temperature (20° C.), may be exposed to temperatures as low as 0° to about 10° below room temperature, and most preferably are maintained at room temperature throughout the blending and forming steps. As such, the actives in the chew mixture and formed treats are not exposed to heats above or below the temperatures stated during performance of the blending and forming steps, whether by admixture with ingredients at temperatures outside the stated ranges, by application of heat generated by a heat source or compression, or by other means. Stability of the actives is therefore preserved during mixing and formation of the edible soft treats, and a well-blended, soft texture is provided.

In general, edible soft chewable medications and treats include as inactive ingredients matter such as binding agents, vitamins, and colors to enhance the manufacturability, texture and appearance of the product. Those of ordinary skill in the art will be familiar with such inactive ingredients, which need not include water for use in the invention. No inedible ingredients are present within the soft treats.

No inactive ingredients of the edible soft chew should be of less than food grade quality and may be of higher quality (e.g., USP or NF grade). In this context, "food grade" refers to material that does not contain or impart chemicals or agents hazardous to health. Thus, a food grade flavoring, if of animal origin, will be one that has been prepared to substantially reduce or eliminate the presence of infectious agents or contaminants therein; e.g., by processes such as pasteurization, pressurization or irradiation.

The latter process in particular can effectively eliminate infectious agents such as *E. coli* O157:H7, *Salmonella* and *Campylobacter* from a wide variety of food and animal-derived substances, such as raw meat products, vegetables, grains and fruits. Preferably, however, edible soft treats of the invention will not contain any animal origin ingredients, and most preferably will not contain any animal origin flavorings. All ingredients should be pharmaceutically acceptable (e.g., food grade, USP or NF, as appropriate).

Flavorings are preferably present in the treats and are at least food grade in quality, and most preferably exclude animal origin flavorings where accepted by the treated species. Preferred non-animal origin flavorings are plant proteins, such as soy protein, to which edible artificial food-like flavorings has been added (e.g., soy-derived bacon flavoring). Depending on the target animal, other non-animal flavorings could include anise oil, carob, peanuts, fruit flavors, sweeteners such as honey, sugar, maple syrup and fructose, herbs such as parsley, celery leaves, peppermint, spearmint, garlic, or combinations thereof.

A particularly preferred flavoring for use in the invention is Provesta™ 356, made by Ohly, Inc. It is a light tan, water-soluble powder that builds on the properties of yeast extracts and reaction flavors to provide a pleasant smoky, cured bacon flavor. Provesta 356 contains no animal derived ingredients.

For administration to horses and other grazing animals, as well as small animals such as rabbits, hamsters, gerbils, and guinea pigs, grains and seeds are especially appealing additional flavoring agents. The grains may be present in any form consistent with the production of the chew including flour, bran, cereal, fiber, whole grain and meal forms, including gluten meals, and may be rolled, crimped, ground, dehydrated or milled. Minerals may also be added as flavorings, such as salt and other spices. Preferably, the grain utilized is dehydrated, milled or flaked. Vegetables such as dehydrated carrots and seeds such as safflower seeds or milo seeds are especially appealing to small animals and may be included.

Further, agents which enhance the manufacturability and texture of a edible soft chew may include softening agents (which may be an anti-sticking agent), an anti-caking agent or lubricant, and a humectant or wetting agent. Illustrative examples of lubricants or anti-caking agents which may be used in the invention include magnesium stearate, calcium stearate, solid polyethylene glycols. If melted, the agents are returned to room temperature +/−10° before admixture with an active, sodium lauryl sulfate, or mixtures thereof. Magnesium stearate is particularly preferred for lubrication and as a component to aid in setting the edible soft treats after molding.

Other additives and excipients are described further herein. For example, glycerin is a preferred humectant useful in maintaining the softness of the edible soft chew over the shelf life of the product. Glycerin is a clear, colorless, odorless, viscous, hydroscopic liquid.

An anti-sticking agent, preferably polyethylene glycol and most preferably PEG 3350 (Dow Chemical), will preferably be included in the edible soft chew mixture before molding at a volume of about 1.0% to 3.0% w/w. After molding, the edible soft treats with the added anti-sticking agent will set-up, usually over a period of 8 to 24 hours for PEG 3350. PEG 3350 congeals quickly, softens the chew mixture, and prevents the edible soft chew units from sticking together after molding.

Softening agents utilized are those which limit density and hardness of the edible soft chew product. Such agents may include polysaccharides and fiber. A polysaccharide may be included in the form of a complex food such as a fruit, a plant starch such as potato or tapioca starch. Polysaccharide may also be provided separately, for example, in the form of chondroitin sulfate or glucosamine HCl.

Fiber may be also provided as filler or as a bulking agent and to provide or maintain porosity in the edible soft chew. Fibers used to this end may be derived from fruits, grains, legumes, vegetables or seeds, or provided in forms such as wood fiber, paper fiber or cellulose fiber such as powdered cellulose fiber. A particularly preferred such bulking agent for use in the invention is bran, such as oat bran.

Binders utilized in edible soft treats may be a sticky substance, but will preferably give the product a food-like texture. A particularly preferred binder is Starch 1500, a pregelatinized starch made by Colorcon Corporation. Pregelatinized starch is a starch that has been chemically and/or mechanically modified to rupture all or part of the starch granules and so render the starch flowable. It contains 5% of free amylase, 15% of free amylopectin and 80% unmodified starch. The source is from corn.

Powdered sugar (sucrose) serves well as a sweetener as well as a binder. Sucrose is obtained from either sugar cane or sugar beets. Salt and/or other spices may be added as appropriate, with salt being especially preferred to enhance flavor.

A preservative such as potassium sorbate, sodium benzoate or calcium propionate may be included in order to retard growth of microorganisms and fungi. Tenox 4 is a combination of BHA and BHT anti-oxidants, made by Eastman Chemicals. It is a preferred and convenient preservation system.

Vitamins may be provided according to the nutritional requirements of the target animal, and may be provided as an element of oils utilized. Vitamins are also present in various oils that may be added as softening agents; for example, canola oil, corn oil, soybean oil and vegetable oil.

For formation of an active suspension, as well as a flavor enhancer and softening agent, oils are utilized. Vegetable oils (such as corn, safflower, cottonseed, soybean and olive oils) are especially preferred, with soybean oil being most preferred.

Excipients that may be utilized include starches, cellulose, or derivatives or mixtures thereof, in amounts ranging, for example, from about 1 to about 60 percent (w/w), preferably from about 2 to about 50 percent, more preferably from about 15 to 50 percent. For example, the excipient may consist of sodium starch glycolate, pregelatinized corn starch (Starch 1500), crospovidone (Polyplasdone XL™, International Specialty Products), and croscarmellose sodium (Ac-Di-Sol™, FMC Corp.), and derivatives thereof.

Excipients may be used to create a trituration of an active. For example, to create a 10% trituration, 100 grams of the active is combined with 900 grams of an excipient, such as a preferred excipient, Starch 1500. Ideally, a geometric dilution of the active is performed, whereby it is first dissolved in a suitable alcohol solvent; e.g., ethyl alcohol. The dissolved active is then combined with the excipient, and the alcohol allowed to evaporate. This step enables a small amount of active to be comprehensively and evenly mixed throughout the starch. The dry mixture is sifted through a screen mesh, fluidized, and is then preferably coated.

If a coating is to be provided (to help protect the stability of the active and mask its taste), food grade coatings are preferred, such as an aqueous film coat from Colorcon Corporation sold as OPADRY™. OPADRY is a methylcellulose based product with a plasticizer and pigment. Since the coating is aqueous based, no special handling precautions are required during manufacture of the edible soft chew. However, after administration, the aqueous film coat will start to erode and/or dissolve within minutes when exposed to water or other liquids in the stomach. Therefore, disintegration and dissolution of the edible soft chew should not be delayed after it is administered to the subject.

The formula described for the exemplary product may be easily modified for delivery of actives to other species. For example, equine edible soft treats may be based on the same basic formula, substituting molasses powder, oat bran and apple for the bacon. Flavorings particularly appealing to cats include artificial soy based compounds with a fish-like flavor. Human recipients may prefer sweeter flavorings, such as sugars or molasses.

3. Processes for Manufacturing a Chewable Dosage Vehicle.

Preferably, a chew mixture formulated as described above, including active and inactive ingredients, is added to a mixing vessel of a mixer capable of blending the material and casting it against the side of the mixing vessels. This action permits the ingredients to be well and consistently blended without application of heat or addition of pharmaceutical grade water to the mixture.

Suitable mixers include horizontal mixers, which generally comprise a mixing chamber, an elongated, horizontal mixing shaft which rotates, and a plurality of mixing tools which depend generally perpendicularly from the horizontal shaft to rotate around the inside of the chamber (see, e.g., U.S. Pat. No. 5,735,603, the disclosure of which is incorporated herein by this reference). The mixing tools are configured and dimensioned as required for the mixing process to follow the shape of the chamber walls as rotated for proper mixing of all of material present. Some such mixing chambers are cylindrically shaped, while others are trough-shaped, such as mixers which are commonly referred to in the art as double-arm mixers or ribbon mixers.

In general, a horizontal mixer will have a horizontal mixing shaft extending out of the chamber at both ends. In a motorized mixer, at one end of the shaft, referred to as the drive end, the shaft is operably coupled to a drive motor for rotating the shaft. At the drive end, the shaft is typically coupled through a bearing structure located between the drive motor and the chamber. The bearing structure provides support of the shaft drive end and also ensures smooth rotation. A separate seal structure is often provided further in along the length of the shaft to seal it against leakage of material into and out of the mixing chamber.

A particularly preferred mixer for use in the invention used is a plough type ribbon mixer with optional agitating blades, sold under the FXM Series™ trademark by Littleford Day Corporation. A 200 kg capacity blender can be used for commercial scale production, and is capable of producing as little as 50 kg of chew mixture for research scale work. No heat is applied during mixing, and the blended product produced has a consistent weight, ingredient distribution and texture from batch to batch.

Preferably, dry ingredients of the chew mixture are blended first, then an oil suspension of the active blended therein, followed by admixture with the liquid ingredients (e.g., humectants and softening agents) to form a thoroughly blended mixture. After blending, the chew mixture is discharged without compression from a port through the blender into a suitable container for processing into individual dosage units with a forming machine.

A variety of forming equipment may be utilized in the invention, but those particularly preferred for use are molding machines developed for use in producing molded food products, such as pre-formed hamburger patties and chicken nuggets. For example, the molding machines disclosed in U.S. Pat. Nos. 3,486,186; 3,887,964; 3,952,478; 4,054,967; 4,097,961; 4,182,003; 4,334,339; 4,338,702; 4,343,068; 4,356,595; 4,372,008; 4,535,505; 4,597,135; 4,608,731; 4,622,717; 4,697,308; 4,768,941; 4,780,931; 4,818,446; 4,821,376; 4,872,241; 4,975,039; 4,996,743; 5,021,025; 5,022,888; 5,655,436; and 5,980,228 (the disclosures of which are incorporated herein) are representative of forming equipment that may be utilized in the invention.

Preferred forming equipment for use in the invention are molding machines that do not apply compression heat to the chew mixture, such as the Formax F6™ molding machine made by the Formax Corporation. The F6 machine has the capabilities of 60 stokes per minute. A square forming die of 6" by 6" can be used to form approximately 16 chunk-like edible soft chew units per stroke, each unit weighing 4 grams and being approximately 5/8" by 5/8" in size. Dies for production of other shapes (e.g., bone shaped treats) may also be utilized.

In such a machine, a rotary valve opens to cause the chew mixture to flow through fill slots beneath into a first set of mold cavities. A mold plate is advanced, forcing the chew mixture into a second set of cavities, then the mold plate is retracted so the cycle can begin again. The molding mechanism is hydraulic, and works by light pressure on the molding plate, without application of heat.

A knockout mechanism is provided with cups that align with the cavities to eject molded mixture from all the mold plate cavities simultaneously. For molding edible soft treats of the invention, such a machine could produce an output per hour of approximately 57,600 units, assuming use of a blender mixture yielding 50,000 units per sub batch. Each batch of treats may be packaged in bulk or, preferably, each chew is then individually packaged for storage.

The invention having been fully described, its practice is illustrated (but not limited) by the following examples. Standard abbreviations and measurements apply throughout the examples unless a contrary definition is given.

EXAMPLE I

Test Animals and Protocols

Test System
   Flea Species: *Ctenocephalides felis*
   Number: ~100 unfed adults per dog per infestation with a sex ratio of ~50/50
   Flea Source: Stillmeadow, Inc. flea colony, Sugarland, Tex.
   Tick Species: *Rhipicephalus sanguineus*
   Number: ~50 unfed adults per dog per infestation (~25 male and ~25 females)
   Tick Source: Ecto Services, Inc., Henderson, N.C.
Host Animals
   Species/Strain/Source: Dog/beagles/Stillmeadow, Inc. dog colony
   Justification of Species: The dog is a target animal
   Age of Animals: Adult
   Body Weights (Pretest): 7.2 to 17.6 kg
   Identification: Tattoos and cage cards
Animal Husbadry
   Cage Type: 3'-4'×4' aluminum pens;
   Housing: Individual
   Environmental Controls Set to Maintain:
   Temperature range of 20°±3° C.
   Humidity range of 30-70%
   12-hour light/dark cycle
   10-12 air changes per hour
   Food: PMI Canine High Density Diet 5L18
   Water Type: Municipal water supply, available ad libitum, analyzed by the Texas Commission on Environmental Quality (TCEQ) Water Utilities Division
   Water System: Water bowl
Protocols
   Body weights were recorded during the pretest period. Six dogs were selected for study, weighed and randomly assigned to two groups of three and infested with either 100 fleas or 50 ticks. For the flea study whose results are shown in Table 3, repeat 100 flea infestations were performed on Days 2 and 5, without additional dosing. For all studies, the Group I dogs served as untreated controls. All animals except those in Group II of the study whose results are reported in Table 1 were dosed orally with the test article in gelatin capsules. The Group II, Table 1 animals received 5 mg of imidacloprid active in a chewable drug delivery vehicle.

For blood collections, drawn blood was collected into lavender top Vacutainer® tubes. The tubes were centrifuged and plasma was drawn off and frozen at approximately −20° C. pending possible future shipment to the sponsor for analysis of levels of test article in the plasma. Comb and pan counts were conducted as noted in the Tables, following dosing. The number of live fleas and ticks removed during the comb counts was recorded as were, where noted in the Tables, dead tick counts.

EXAMPLE II

Efficacy of Oral Imidacloprid Against Flea and Tick Infestations

In general, orally dosed imidacloprid was 100% efficacious against pre-existing *C. felis* infestations when dosed at a rate as low as 0.25 mg/kg. Increasing dosage therefore did not increase efficacy against an initial infestation. However, increasing initial dosage levels substantially improved resistance to reinfestation, especially at 5 days following administration of the dose.

For use against *R. sanguineus* ticks, increasing dosage beyond a threshold level tested (3 mg/kg) had the counter-intuitive effect of not improving (at the 22 and 30 mg/kg levels) or even reducing (at 10 and 15 mg/kg levels) efficacy, although efficacy could slightly improve over days following initial dosing. Therefore, relatively low doses of oral imidacloprid (e.g., 3 mg/kg) suffice to substantially control tick infestations, while higher (but still sub-toxic) dosages may optionally be utilized where the risk of reinfestation is significant

TABLE 1

Flea Counts and Results (Dose as Low as 0.25 mg/kg).

| Animal Number | 1 hour pan counts | 3 hour pan counts | Comb Count Day 1 | Mean Efficacy |
|---|---|---|---|---|
| Group I - Untreated | | | | |
| 4113-M | 1 | 0 | 19 | |
| 4115-M | 0 | 0 | 65 | |
| 4144-F | 0 | 0 | 70 | |
| Mean | 0.0 | 0.0 | 56.3 | NA |
| S.D. | 0.0 | 0.0 | 14.4 | |
| Group II - Imidacloprid Oral 0.25 mg/kg | | | | |
| 3652-M | 0 | 2 | 0 | |
| 3949-M | 0 | 9 | 0 | |
| Mean | 0.0 | 5.5 | 0.0 | 100.0 |
| S.D. | 0.0 | 17.1 | 0.0 | |
| Group II - Imidacloprid chewable (5.0 mg to animals 4-20 lbs) | | | | |
| 4114-M | 0 | 14 | 0 | |
| 4141-F | 0 | 25 | 0 | |
| 4142-F | 1 | 18 | | |

TABLE 1-continued

Flea Counts and Results (Dose as Low as 0.25 mg/kg).

| Animal Number | 1 hour pan counts | 3 hour pan counts | Comb Count Day 1 | Mean Efficacy |
|---|---|---|---|---|
| Mean | 0.3 | 19.0 | 0.0 | 100.0 |
| S.D. | 0.6 | 5.6 | 0.0 | |

TABLE 2

Flea Counts and Results (Dose at 0.5 and 1.0 mg/kg).

| Animal Number | 4 hour pan counts | # Live Fleas Removed | 6 hour pan counts | # Live Fleas Removed | Mean Efficacy |
|---|---|---|---|---|---|
| Group I - Untreated | | | | | |
| 4163-M | 0 | 56 | 0 | 52 | |
| 4164-M | 2 | 50 | 0 | 35 | |
| 4174-F | 0 | 51 | 0 | 49 | |
| Mean | 0.0 | 52.3 | 0.0 | 45.3 | NA |
| S.D. | 0.0 | 0.0 | 0.0 | 9.1 | |
| Group II - Imidacloprid Oral 0.5 mg/kg | | | | | |
| 4162-M | 5 | 31 | 39 | 0 | |
| 4166-M | 45 | 2 | 33 | 0 | |
| 4173-F | 15 | 35 | 47 | 0 | |
| Mean | 0.0 | 22.7 | 39.7 | 0.0 | 100.0 |
| S.D. | 0.0 | 18.0 | 7.0 | 0.0 | |
| Group II - Imidacloprid Oral 1.0 mg/kg | | | | | |
| 4161-M | 44 | 4 | 35 | 0 | |
| 4171-F | 41 | 12 | 44 | 0 | |
| 4177-F | 40 | 11 | 53 | 0 | |
| Mean | 41.7 | 9.0 | 44.0 | 0.0 | 100.0 |
| S.D. | 2.1 | 4.4 | 9.0 | 0.0 | |

TABLE 3

Flea Counts and Results (Doses at 3, 6 and 10 mg/kg).

| Animal Number | Average 1 hour pan counts | Average 3 hour pan counts | Comb Count Day 1 | Comb Count Day 2 (reinfested) | Comb Count Day 5 (reinfested) |
|---|---|---|---|---|---|
| Group I - Untreated | | | | | |
| 3767-M | 1 | 0 | 70 | 19 | 19 |
| 4086-M | 0 | 0 | 65 | 65 | 65 |
| 3886-F | 0 | 0 | 40 | 70 | 70 |
| Mean | 0.0 | 0.0 | 58.3 | 56.3 | 56.3 |
| | | | NA | NA | NA |
| Group II - Imidacloprid Oral 3.0 mg/kg | | | | | |
| 2859-M | 2 | 7 | 0 | 15 | 32 |
| 3880-M | 1 | 9 | 0 | 40 | 80 |
| 3045-F | 1 | 11 | 0 | 12 | 42 |
| Mean | 1.3 | 9.0 | 0.0 | 22.3 | 25.3 |
| Efficacy | — | — | 100.0 | 68.1 | 42.1 |
| Group III - Imidacloprid Oral 6.0 mg/kg | | | | | |
| 3184-M | 5 | 13 | 0 | 0 | 7 |
| 3895-F | 6 | 22 | 0 | 0 | 17 |
| 3896-F | 12 | 27 | 0 | 0 | 31 |
| Mean | 7.6 | 19.6 | 0.0 | 0.0 | 12.1 |
| Efficacy | — | — | 100.0 | 100.0 | 79.3 |
| Group IV - Imidacloprid Oral 10.0 mg/kg | | | | | |
| 3171-F | 10 | 14 | 0 | 0 | 0 |
| 3175-F | 16 | 25 | 0 | 0 | 5 |
| 3897-F | 8 | 18 | 0 | 0 | 1 |
| Mean | 11.3 | 19.0 | 0.0 | 0.0 | 2.0 |
| Efficacy | — | — | 100.0 | 100.0 | 97.7 |

TABLE 4

Tick Counts and Results (Doses at 3 and 10 mg/kg).

| Number | Ticks Removed Day 2 | Attached Dead Day 2 | Mean Efficacy | Live Attached Day 6 | Dead Attached Day 6 | Live Free Day 6 | Dead Free Day 6 | Efficacy |
|---|---|---|---|---|---|---|---|---|
| Group I - Untreated ||||||||||
| 2923 | 21 | 0 |  | 9 | 1 | 0 | 0 |  |
| 3176 | 25 | 0 |  | 33 | 0 | 0 | 0 |  |
| 3180 | 17 | 1 |  | 17 | 0 | 0 | 0 |  |
| Mean | 21 | 0 |  | 20 | 0 | 0.0 | 0.0 |  |
| S.D. | 4 | 1 | NA | 12 | 1 | 0.0 | 0.0 | NA |
| Group II - Imidacloprid Oral 3 mg/kg ||||||||||
| 2922 | 17 | 1 |  | 6 | 2 | 1 | 0 |  |
| 2942 | 8 | 1 |  | 4 | 2 | 0 | 0 |  |
| 3196 | 28 | 0 |  | 13 | 0 | 0 | 0 |  |
| Mean | 18 | 1 |  | 8 | 0 | 0 | 0.0 |  |
| S.D. | 10 | 1 | 15.9 | 5 | 1 | 1 | 0.0 | 61.0 |
| Group III - Imidacloprid Oral 10 mg/kg ||||||||||
| 2849 | 16 | 2 |  | 14 | 1 | 1 | 0 |  |
| 3943 | 22 | 0 |  | 8 | 0 | 0 | 0 |  |
| 3194 | 23 | 6 |  | 28 | 0 | 0 | 0 |  |
| Mean | 20 | 3 |  | 17 | 0 | 0 | 0 |  |
| S.D. | 4 | 3 | 3.2 | 10 | 1 | 1 | 0 | 15.3 |

TABLE 5

Tick Counts and Results at Day 1 (Doses at 15, 22 and 30 mg/kg).

| Animal | Live Ticks | Dead Ticks | Mean Efficacy |
|---|---|---|---|
| Group I - Untreated ||||
| 3172 | 26 | 0 |  |
| 3582 | 30 | 0 |  |
| 3583 | 32 | 0 |  |
| Mean | 29 | 0 |  |
| S.D. | 3 | 0 | NA |
| Group II - Imidacloprid Oral at 15 mg/kg ||||
| 3170 | 33 | 0 |  |
| 3201 | 2 | 3 |  |
| 3581 | 10 | 1 |  |
| Mean | 15 | 1 |  |
| S.D. | 16 | 2 | 48.9 |
| Group II - Imidacloprid Oral at 22 mg/kg ||||
| 3356 | 3 | 2 |  |
| 3357 | 12 | 1 |  |
| 3529 | 13 | 0 |  |
| Mean | 9 | 1 |  |
| S.D. | 6 | 2 | 68.2 |
| Group II - Imidacloprid Oral at 30 mg/kg ||||
| 3197 | 10 | 7 |  |
| 3200 | 12 | 0 |  |
| 3210 | 11 | 0 |  |
| Mean | 11 | 2 |  |
| S.D. | 1 | 4 | 62.5 |

TABLE 6

Tick Counts and Results at Days 2 and 3 (Dose at 30 mg/kg).

| Animal | Hand Count Day 2 | Comb Count Day 3 Live | Comb Count Day 3 Dead | Mean Efficacy |
|---|---|---|---|---|
| Group I - Untreated |||||
| 3353-M | Not done | 27 | 0 |  |
| 3172-M | Not done | 28 | 0 |  |
| 3582-F | Not done | 18 | 0 |  |
| Mean | — | 24 | 0 |  |
| S.D. | — | 6 | 0 | NA |
| Group II - Imidacloprid Oral at 30 mg/kg |||||
| 3197-M | 8 | 6 | 0 |  |
| 3200-M | 13 | 5 | 2 |  |
| 3201-F | 7 | 4 | 0 |  |
| Mean | 9 | 5 | 1 |  |
| S.D. | 3 | 1 | 1 | 79.5 |

The invention having been fully described, those of ordinary skill in the art will recognize that it extends to equivalents and modifications thereof, without departing from the scope of the invention, which is defined by the appended claims.

What is claimed is:

1. A method for treating an infestation of fleas on a cat or dog the method comprising
    orally administering to the cat or dog
    once per infestation
    a single dose
    of a parasiticidal composition that is a solid dosage form and
    comprises imidacloprid,
    wherein the dose contains from 0.25 mg to 10 mg of imidacloprid per kg of body weight of the cat or dog and
    imidacloprid is the only compound present in the parasiticidal composition effective against fleas, and
    wherein the infestation is eliminated within 24 hours.

2. The method of claim 1, wherein the dose contains from 0.5 mg to 6 mg of imidacloprid per kg of body weight of the cat or dog.

3. The method according to claim 1, wherein the dosage form is a chewable.

4. The method of claim 1, wherein the dosage form is a pill, tablet or capsule.

5. The method according to claim 1, wherein the fleas are adult fleas.

6. The method according to claim 1, wherein the fleas are larvae or flea eggs.

7. The method of claim 1, wherein the oral administering is to a dog.

8. The method of claim 1, wherein the parasiticidal composition further comprises a flavoring.

9. The method of claim 3, wherein the parasiticidal composition further comprises a flavoring.

10. A method for treating an infestation of ticks on a cat or dog, the method comprising orally administering to the cat or dog once per infestation a single dose of a parasiticidal composition that is a solid dosage form and comprises imidacloprid, wherein the dose contains from 15 mg to 30 mg of imidacloprid per kg of body weight of the cat or dog and imidacloprid is the only compound present in the parasiticidal composition effective against ticks, and wherein the infestation is eliminated within 72 hours.

11. The method of claim 10, wherein the dose contains from 22 mg to 30 mg of indacloprid per kg of body weight of the cat or dog.

12. The method according to claim 10, wherein the dosage form is a chewable.

13. The method of claim 10, wherein the dosage form is a pill, tablet or capsule.

14. The method according to claim 10, wherein the ticks are adult ticks or tick nymphs.

15. The method according to claim 10, wherein the ticks are tick larvae or tick eggs.

16. The method of claim 10, wherein the oral administering is to a dog.

17. The method of claim 10, wherein the parasiticidal composition further comprises a flavoring.

18. The method of claim 12, wherein the parasiticidal composition further comprises a flavoring.

19. The method of claim 10, wherein the infestation is eliminated within 24 hours.

20. The method of claim 2, wherein the solid dosage form is a soft chewable treat, and where the oral administering is to a dog, and wherein the composition comprises a flavoring.

* * * * *